United States Patent [19]

Hirsch

[11] 4,041,607

[45] Aug. 16, 1977

[54] COMPOSITION AND METHOD FOR FORMING DENTAL RESTORATIONS

[76] Inventor: Arie L. Hirsch, 2241-16th Ave., San Francisco, Calif. 94116

[21] Appl. No.: 680,401

[22] Filed: Apr. 26, 1976

[51] Int. Cl.² ............................................. A61C 13/00
[52] U.S. Cl. .......................................................... 32/8
[58] Field of Search .................................... 32/2, 12, 8

[56] References Cited

U.S. PATENT DOCUMENTS

| | | | |
|---|---|---|---|
| 3,052,982 | 11/1962 | Weinstein et al. | 32/8 |
| 3,834,024 | 9/1974 | Kochaui | 32/8 |

Primary Examiner—Robert Peshock
Attorney, Agent, or Firm—Townsend and Townsend

[57] ABSTRACT

Novel use of a certain nickel chromium alloy in dental restorations.

2 Claims, No Drawings

COMPOSITION AND METHOD FOR FORMING DENTAL RESTORATIONS

This invention relates to dental restorations. More particularly, it relates to the novel use of an alloy imparting to the restorations made therewith a number of advantageous properties.

Dental restorations and the use of non-precious alloys of the present type in their fabrication are disclosed in the following patents: U.S. Pat. Nos. 3,464,817; 3,716,418; 3,749,570; 3,761,728; 3,834,024; 2,162,253; 2,295,864; 2,506,526; German Patent No. 2,106,013.

The present invention employs as an alloy the following composition:

| Limiting Chemical Composition, % Weight | | |
|---|---|---|
| | Min. | Max. |
| Nickel (+ Cobalt) | 72.0 | |
| Carbon | | 0.15 |
| Manganese | | 1.00 |
| Iron | 6.00 | 10.00 |
| Sulfur | | 0.015 |
| Silicon | | 0.50 |
| Copper | | 0.50 |
| Chromium | 14.00 | 17.00 |

This material is available under the Trademark INCONEL Alloy 600.

The alloy of this invention is used in making dental restorations, preferably in crown and bridge applications, in accordance with well-known procedures. The present invention is based on the discovery that the above defined alloy can be substituted for those non-precious alloys heretofore conventionally used and several important improvements are obtained. More particularly, using the present alloy in otherwise conventional procedures for making dental restorations will result in the technician having an easier task during any required soldering. The present alloy is softer than previously used similar alloys and it is, therefore, easier to work and to fabricate the restoration.

Other very substantial practical advantages of the present alloy are that the alloy will receive and firmly bond with any porcelain. Heretofore the previously used analogous alloys were limited by the fact that only certain porcelains could be effectively coated thereon. The present alloy does not have this limitation.

Another very substantial advantage gained in the present invention is that the porcelain selected forms a stronger bond with the alloy.

Finally, a significant advantage is obtained in that the present alloy has a lower melting point than the previously used analogous alloys. As a result, the heating apparatus utilized in melting the alloy preparatory to casting can be more conveniently selected. For example, with the present alloy it is possible to melt a pellet for casting utilizing a torch fueled with natural gas and oxygen. This is the same type of a torch commonly found and used in dental laboratories for working with precious metals such as gold. In distinction, some previously used non-precious alloys have required the use of acetylene torches, the combustion of which creates undesirable pollution such as carbon particles and soot.

As mentioned above, the present invention is essentially completely compatable with prior procedures and involves simply the substitution of the above defined alloy for those described in the prior art. Reference is particularly made to three U.S. patents to Jocob Kochavi, namely: U.S. Pat. No. 3,834,024; 3,716,418 and 3,761,728, the disclosures of which are incorporated herein by reference. These three U.S. patents disclose the use of a nickel-chromium alloy similar to the present one and relative to which the present alloy exhibits the above noted improvements. The present alloy can be substituted and worked in accordance with the specific embodiments and procedures of these patents to Kochavi. A preferred sequence of steps in utilizing the present alloy for forming, for example, a crown and bridge dental restoration is as follows:

A. Waxing and Spruing

With linqual collar: Wax using the same conventional techniques used for gold and porcelain bridge work. Sprue to the lingual collar or interproximal strut.

With conventional sprue technique: Use 8 gauge sprue direct from button to wax pattern. The sprue should be no longer than ¼-inch.

With feed sprue technique: Use an 8 gauge feed with an 8 gauge sprue, with the distance between feed sprue and wax pattern no more than ¼-inch.

B. Investing

Use any high heat ceramic crown and bridge investment, utilizing manufacturer's instructions to determine powder to liquid ratio. For additional expansion, increase amount of liquid. Line the ring with a wet asbestos liner. Investment should be approximately ¼-inch in thickness above wax patterns. Scrape away glazed surface that forms at end of investment before placing into burnout furnace.

C. Burnout

Inlay size rings: Place ring into furnace, on ring supports, between 0° F and 900° F. Increase temperature at moderage rate to 1600° F and heat soak at this temperature for 1 hour.

Larger rings: Same as above, but heat soak for a proportionately longer time, according to size of ring.

D. Casting with Natural Gas and Oxygen

For best results, preheat crucible in burnout oven when burning out ring. Do not preheat alloy. Wind the casting machine to its maximum. Remove preheated crucible from oven and place in casting machine. For best results, use a multi-orifice gas oxygen torch. Adjust flame as follows: Open gas all the way. Adjust oxygen to develop an inner cone approximately ½-inch in length. Place virgin metal in bottom of crucible. If button is being used, place button on top of virgin metal. Apply the hot inner cone tip of the flame to the metal circulating flame for even heating until metal collapses.

E. Removing Casting from Ring

When redness has disappeared, quench ring. Cut investment from both ends of rings to asbestos liner. Remove casting and turn away bulk. Dry and sand blast at high pressure. Finish using silicone bonded stones, then dip in ammonia and rinse in clean tap water. Degassing: Place in oven at 1600° F to 1875° F with vacuum, then remove immediately.

F. Preparing Alloy for Porcelain Application

Sand blast with aluminum oxide ($AlO_2$). Place in ammonia for one minute, then rinse in running water.

G. Opaquing

After rinsing, apply opaque to clean casting and fire under vacuum from 1200° F till 1825° F, hold vacuum 1 minute. For better results, apply a second opaque. Fire under vacuum from 1200° F till 1750° F, then break vacuum till 1825° F. Remove hot bridge from furnace.

H. Porcelain Bake

Build-up, fire and glaze, following instructions provided by porcelain manufacturer. Fire porcelain to complete maturity. After firing cycle is completed, move bridge from muffle to the vestibule to furnace until the redness darkens. Then place the bridge at room temperature.

I. Cleaning and Polishing

Use Pasche air brush to clean inside of castings. Polish using standard procedures.

What is claimed is:

1. In a dental restoration having a metal frame the improvement comprising: forming said metal frame from an alloy of the composition

|  | Weight % | |
| --- | --- | --- |
|  | Min. | Max. |
| Nickel (+ Cobalt) | 72.0 |  |
| Carbon |  | 0.15 |
| Manganese |  | 1.00 |
| Iron | 6.00 | 10.00 |
| Sulfur |  | 0.015 |
| Silicon |  | 0.50 |
| Copper |  | 0.50 |
| Chromium | 14.00 | 17.00 |

2. An improved dental restoration in accordance with claim 1 wherein said metal frame has a dental porcelain layer bonded thereto.

* * * * *